United States Patent [19]

Kerouac

[11] 4,057,051
[45] Nov. 8, 1977

[54] HAND HELD EAR TEST PROBE

[75] Inventor: Adrian R. Kerouac, Litchfield, N.H.

[73] Assignee: American Electromedics Corporation, Acton, Mass.

[21] Appl. No.: 645,082

[22] Filed: Dec. 29, 1975

[51] Int. Cl.² .............................................. A61B 5/12
[52] U.S. Cl. .................................... 128/2 Z; 73/573; 73/585
[58] Field of Search ............... 128/2 R, 2 Z; 73/67.1, 73/69, 553; 179/1 N

[56] References Cited

U.S. PATENT DOCUMENTS

| | | | |
|---|---|---|---|
| 3,440,867 | 4/1969 | Prall et al. | 128/2 R |
| 3,757,769 | 9/1973 | Arguimbau et al. | 128/2 Z |
| 3,882,848 | 5/1975 | Klar et al. | 128/2 Z |

Primary Examiner—William E. Kamm
Attorney, Agent, or Firm—Holland, Armstrong, Wilkie & Previto

[57] ABSTRACT

A hand held ear test probe is disclosed for use in clinical evaluations of hearing problems. There are a number of important tests for evaluating hearing system losses which are based upon measurements taken in patients' external ear canals using a test probe. A probe is described for such tests which is inserted in the patient's ear and which is hand held by the clinician without the use of head bands or other probe supports. The hand held probe has a shaped outer casing which supports the probe and the related ear sealing and pressurizing means as well as the transducers for the transmitted and received audio test signals.

4 Claims, 8 Drawing Figures

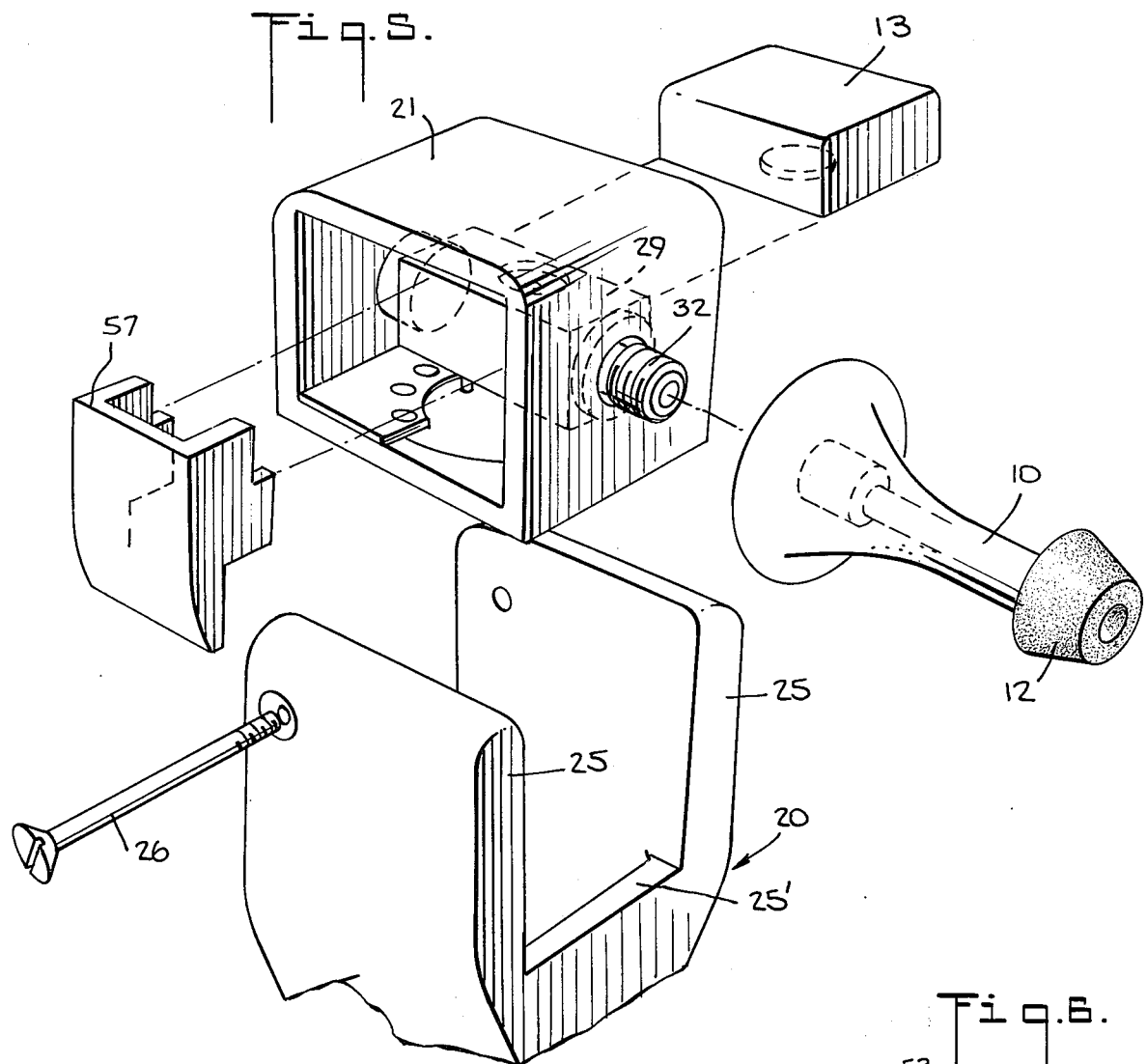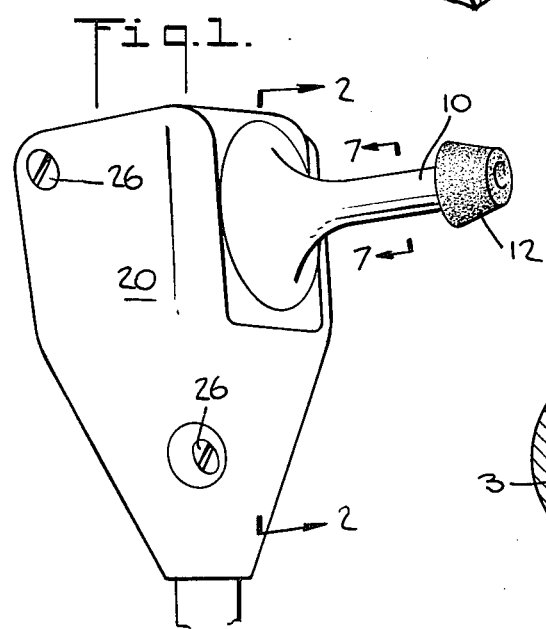

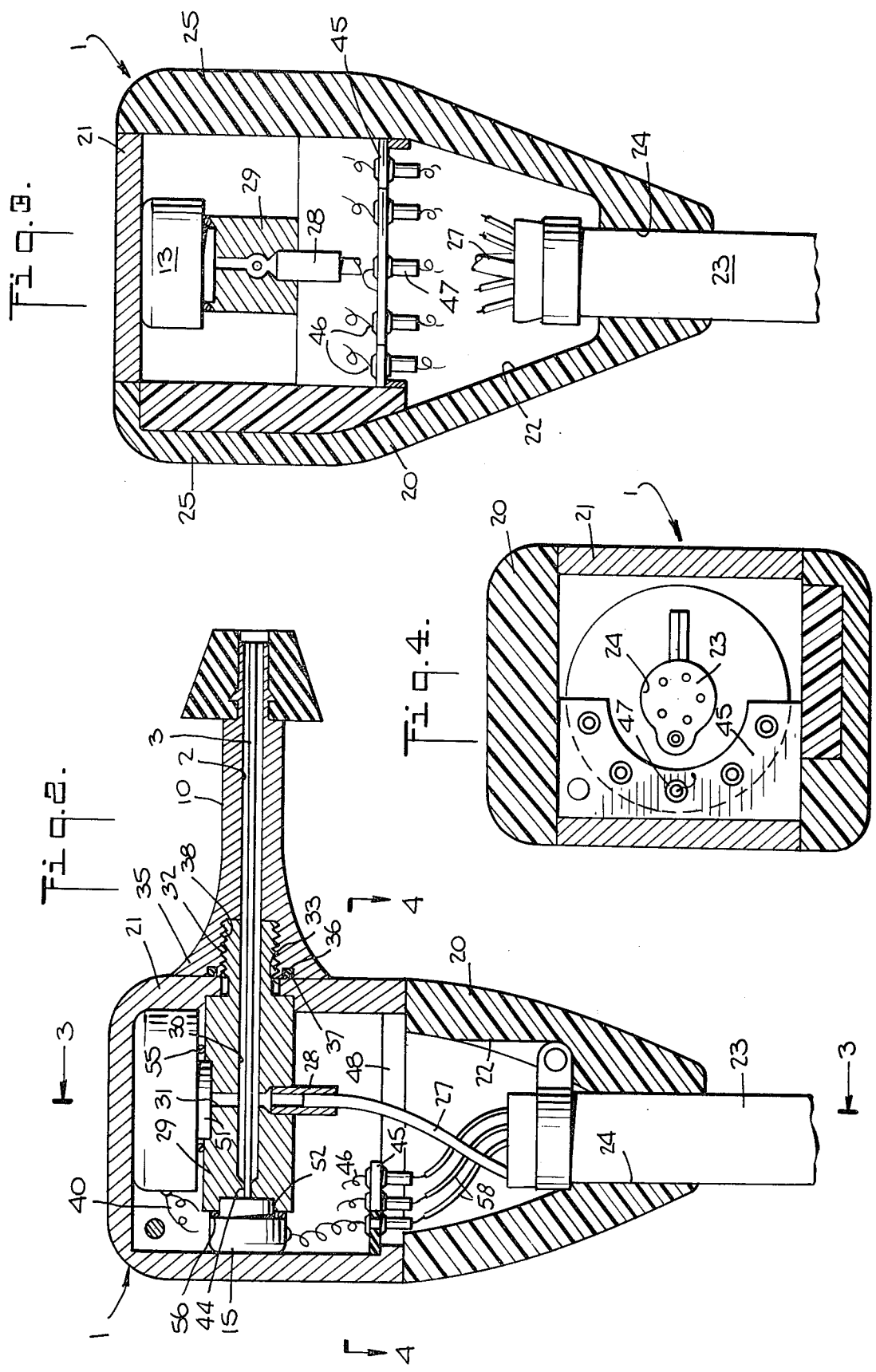

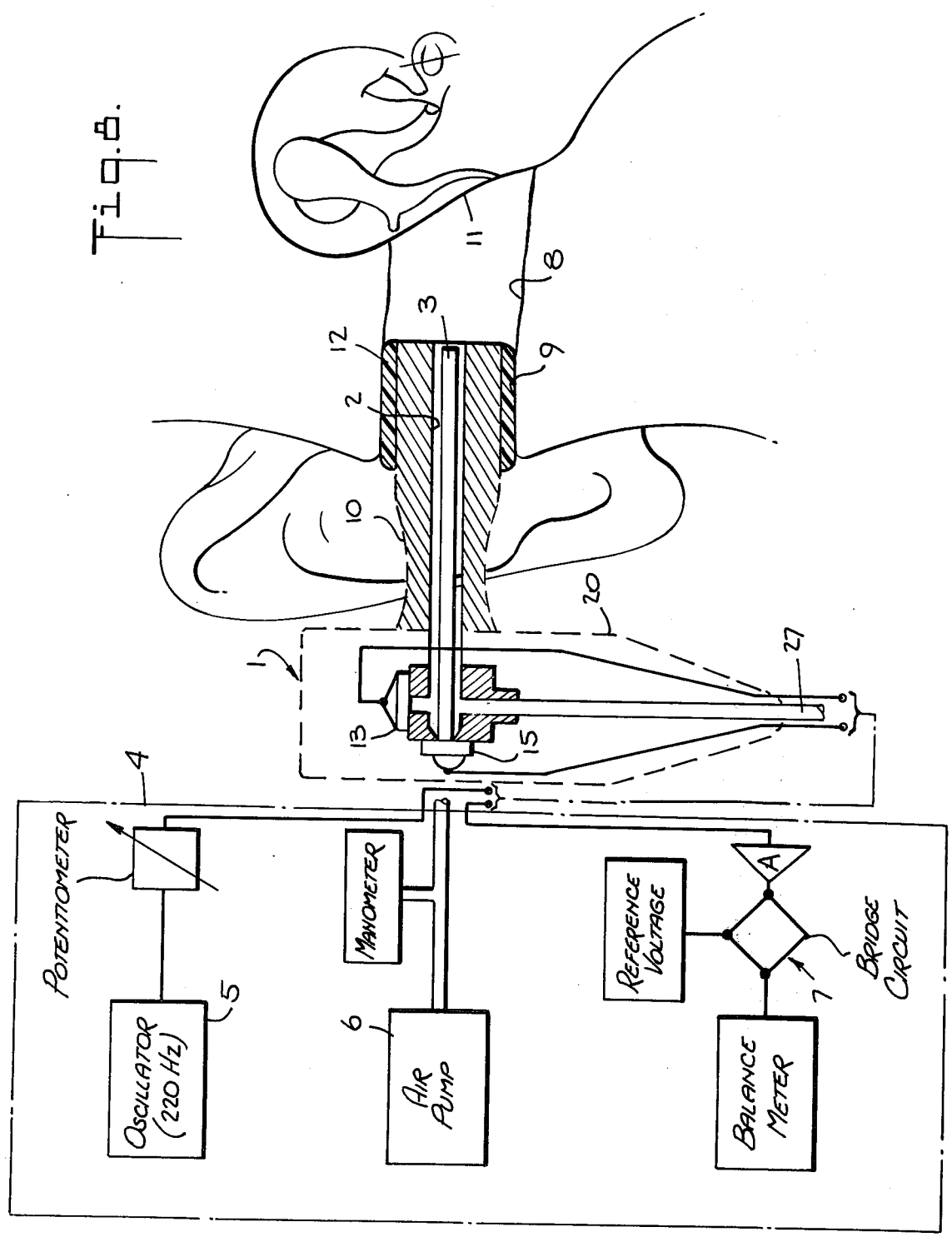

HAND HELD EAR TEST PROBE

BACKGROUND OF THE INVENTION

The present invention relates to clinical evaluation of hearing loss and more particularly to an improved hand held test probe for use with ear test equipment.

One test procedure for evaluating hearing losses, for example, is known as Acoustic Impedance Testing or Impedance Audiometry. This test procedure uses acoustical measurements made within the patient's outer ear canal and includes the step of closing off the ear canal adjacent to the patient's tympanic membrane with a probe. The probe forms an air seal for permitting the control of the air pressure within the sealed cavity and the transmission to and receipt of sound signals from the closed cavity.

The equipment for these tests is known and has been used heretofore with a number of ear probes for accomplishing the above results. The probe of the present invention is improved whereby it may be hand held by the clinician permitting the tests to be done quickly and conveniently without adjustment of head bands or other supports, particularly in the case of children and certain other patients having a short attention span or an inability to cooperate in the test procedures.

Accordingly, an object of the present invention is to provide improved equipment for clinical evaluations of hearing losses or other ear problems.

Another object of the present invention is to provide a hand held test probe for clinical ear testing.

Another object of the present invention is to provide an improved hand held test probe or rugged, convenient and efficient form.

Other and further objects of the invention will be obvious upon an understanding of the illustrative embodiment about to be described or will be indicated in the appended claims, and various advantages not referred to herein will occur to one skilled in the art upon employment of the invention in practice.

BRIEF DESCRIPTION OF THE DRAWING

A preferred embodiment of the invention has been chosen for purposes of illustration and description and is shown in the accompanying drawing forming a part of the specification, wherein:

FIG. 1 is a perspective view of a preferred embodiment of a hand held probe in accordance with this invention.

FIG. 2 is a vertical sectional view taken along line 2—2 on FIG. 1.

FIG. 3 is a vertical sectional view taken along line 3—3 on FIG. 2.

FIG. 4 is a horizontal sectional view taken along line 4—4 on FIG. 2.

FIG. 5 is an exploded perspective view of the probe.

FIG. 6 is an enlarged detailed perspective view of the transfer case transducer mounter.

FIG. 7 is a horizontal section view taken along line 7—7 on FIG. 1.

FIG. 8 is a diagrammatic illustration of the hand held probe in its test position forming a sealed test cavity in the patient's ear canal.

DESCRIPTION OF THE PREFERRED EMBODIMENT

This invention relates particularly to a hand held probe as used in performing a number of tests in connection with a clinical evaluation of hearing losses or other problems. The following description will refer to typical tests in a general way, particularly with reference to FIG. 8 to provide a background for the description of the elements of the probe and its improved features. The hand held probe, for example, is used in acoustic impedance tests in the setup illustrated diagrammatically in FIG. 8.

FIG. 8 illustrates the hand held probe used with test equipment for a test known as Tympanometry. This test uses a probe 1 in accordance with the invention including conduits 2 and 3 for coupling an impedance audiometer 4 including oscillator 5, an air pump 6, and a signal response measuring device in the form of an acoustic bridge 7 to a closed-off cavity 8 within the patient's ear canal 9. FIG. 8 illustrates the probe 1 in accordance with the present invention held at the patient's ear canal 9 so that the ear tube 10 closes off and hermetically seals the cavity 8 within the canal 9 and adjacent to the ear tympanic membrane 11. As resilient cuff 12 on the ear tube 10 is positioned on the inner end of the tube 10 for forming the air-tight or hermetic seal with the canal 9 walls.

The tympanometric test provides for the transmission of a sound signal wave of a predetermined frequency and volume from the oscillator 5 and loud speaker 13 through one of the probe conduits 2 to the sealed-off cavity 8. The testing involves the supply of this sound signal to the cavity 8 with the tympanic membrane 11 being stressed or conditioned by the adjustment of the air pressure within the sealed cavity 8 by means of the air pump 6 and a manometer 14. The air source is also coupled to the sealed cavity 8 through the conduit 2 within the probe 1. The tympanometric measurements are made for determining ear drum compliance changes as the air pressure is altered within the sealed cavity 8. These changes are measured by use of the second conduit 3 within the probe 1 which conducts sound signals from the cavity 8 to a microphone transducer 15 and then as an electrical signal to the measuring bridge 7.

The hand held probe 1 performs the initial functions of sealing off a cavity 8 within the ear canal 9 of appropriate volume and of also coupling the several conduits 2 and 3 to the cavity 8 while the cavity 8 air pressure is adjusted for the test.

Probes 1 also are used in a generally similar way for forming cavities 8 with varying air pressures for Static Compliance Testing and for Acoustic Reflex Threshold tests. In the Static Compliance Test, which measures the middle ear system mobility, a condition of the testing also requires a setting and an adjustment of air pressure within the sealed-off ear canal 8 in the manner already described.

IMPROVED HAND HELD PROBE

FIGS. 1 through 7 illustrate a preferred embodiment of the hand held probe of the invention. FIG. 1 shows the probe 1 including a molded plastic casing 20 which supports the acoustic and air pressure elements and which has a generally conical lower portion which provides a convenient hand grip for the clinician. The upper portion of the casing 20 provides a rigid support for the ear tube 10 by mounting a hollow tube supporting metal frame 21. The metal frame 21 also mounts a transducer and the air pressure elements as well as rigidly supporting the outwardly extending ear tube 10 which has a resilient sealing tube or cuff 12 releasably attached to its outer end.

FIGS. 2, 3 and 4, which are sectional views of the shaped plastic casing 20, illustrate a hollow generally conicial lower portion 22 which receives the wire and air tube cable 23 through an aperture 24. The cross-section of the aperture 24 is shaped to conform generally to the particular shape of the cable 23 as, for example, the rounded and irregular cross-sectional shape illustrated at 24 in FIG. 4. For convenience of assembly, the plastic casing 20 is preferably formed in two complementary and generally similar sections. The upper portion of the plastic casing 20 includes spaced flange members 25 which cooperate to provide a support nest 25' for the hollow metal frame 21 as best illustrated in FIG. 5.

The metal frame 21 is proportioned to fit snugly into the nest 25' of the casing 20 and the two sections of the casing 20 are locked together and the metal frame 21 is held in position by a pair of bolts 26 which pass through suitable apertures in one section of the casing 20 and which engage suitable threaded apertures in the other section of the casing 20.

As described above, the probe 1 is used to seal off the outer ear canal 9 and to admit air into the sealed canal 9 to establish a predetermined air pressure in the sealed canal 9. Air is fed to the probe through a hollow tube 27 included in the probe cable 23. The inner end of the tube 27 is coupled to an air inlet 28 in a transfer case 29.

The case 29 includes a central conduit 30 at right angles to a second bore 31 associated with the air inlet 28. The first conduit 30 extends through a threaded coupling flange 32 which projects through an aperture 33 in the metal frame 21. The air conduit 30 within the transfer case 29 is aligned to communicate with a central conduit 2 within the ear tube 10. As illustrated in FIGS. 2 and 5, the ear tube 10 has a flared inner end 35 including an 0-ring sealing groove 36 for an 0-ring 37. A threaded socket 38 on the tube 10 affixes it to the transfer case 29 and rigidly affixes the transfer case 29 and the metal frame 21 together.

A number of electrical circuits are provided in the probe 1 which are coupled to feed an audio frequency electrical signal into the probe 1 and to receive a portion of that signal back from the sealed ear cavity 8. A pair of input wires 40 are coupled to a transmitter or sound transducer 13 mounted on top of the transfer case 29. The transmitter 13 converts the electrical signal to audio sound waves and couples this sound signal to the sealed cavity 8 through a channel comprising the bores 30 and 31 in the transfer case 29 and the conduit 2 in the ear tube 10.

A second transducer or receiver 15 is mounted at the back of a transfer case 29. The transducer 15 receives a signal from the sealed cavity 8 through a central or inner tube 3 positioned within the air conduit 2 and mounted in an aperture 44 at the rear end of the transfer case 29. The receiver transducer 15 converts the sound signal within the inner tube 3 into an electrical signal which is fed to the above described test equipment through additional wires 58 in the probe cable 23. A suitable terminal board 45 includes terminals 46 for the above described electrical signals and a ground terminal 47 coupled to the metal frame 21 is attached to the bottom portion 48 of the metal frame 21.

As best illustrated in FIG. 6, acoustic seals are provided between the above mentioned transducers and the transfer case 29 by providing generally circular coupling flanges 51 and 52 and cooperating circular cavities 53 and 54 on the case 29 together with compressed sealing rings 55 and 56 surrounding the flanges 51 and 52.

One or more bosses, such as illustrated at 57 in FIG. 5, are shaped to fit within the metal frame 21 and to lock the transducers 13 and 15 and the transfer case 29 in position within the metal case 21 and between the flange members 25 of the casing 20.

In use, the hand held probe 1 is prepared for test by positioning a fresh and sterile cuff 12 on the outer end of the probe tube 10. A clinician now grips the probe 1 by the handle portion 22 and positions the cuff 12 within the patient's ear canal 9. A seal is made with the ear canal 9 walls to form an airtight cavity at the inner end of the ear canal 9. It is only necessary for the clinician to lightly retain the probe 1 in the sealed position while he then adjusts the air pressure and proceeds with the acoustic testing. Upon completion of the test, the probe 1 is instantly removed from the ear and may be made ready for and inserted into the next patient's ear almost immediately thereby eliminating the time consuming steps associated with prior head band supported or other types of probes.

It will be seen that an improved probe has been provided which is adapted for hand held use and which thereby provides for fully satisfactory acoustic testing of a patient's hearing with a decrease in the manipulations required by the clinician. This results in a reduction in the required test time as well as providing increased comfort for the patient being tested.

As various changes may be made in the form, construction and arrangement of the parts herein without departing from the spirit and scope of the invention and without sacrificing any of its advantages, it is to be understood that all matter herein is to be interpreted as illustrative and not in a limiting sense.

Having thus described my invention, I claim:

1. An improved ear test probe comprising the combination of:
   an ear tube support including a lower tapered hand gripping portion and an upper hollow portion;
   an ear tube projecting from the upper hollow portion of said support;
   a plurality of conduits in said ear tube;
   a transfer case in said upper hollow portion;
   air coupling means in said transfer case to couple one of said conduits to a source of air under pressure; and
   a transmitter transducer coupled to one conduit in said air tube by said transfer case and a receiver transducer coupled to another conduit in said ear tube by said transfer case.

2. The probe as claimed in claim 1 in which said hollow upper portion comprises a metal frame support for said ear tube.

3. The probe as claimed in claim 1 in which one of said conduits in said ear tube comprises an inner tubular member positioned within a second of said conduits in said ear tube and extending into one of said conduits in said transfer case.

4. The probe as claimed in claim 1 which further comprises means on said ear tube for releasably mounting a resilient ear canal sealing member.

* * * * *